United States Patent [19]
Nakamura et al.

[11] Patent Number: 5,172,421
[45] Date of Patent: Dec. 15, 1992

[54] AUTOMATED METHOD OF CLASSIFYING OPTICAL FIBER FLAWS

[75] Inventors: Alan M. Nakamura, Torrance; Teresa M. Silberberg, Agoura; Michael R. S. Vince, Thousand Oaks; Theodore Carmely, Van Nuys, all of Calif.

[73] Assignee: Hughes Aircraft Company, Los Angeles, Calif.

[21] Appl. No.: 676,058

[22] Filed: Mar. 27, 1991

[51] Int. Cl.⁵ .................. G06K 9/00; G01B 11/08
[52] U.S. Cl. .................. 382/8; 356/73.1; 65/29; 250/562
[58] Field of Search .......... 356/73.1, 384, 430, 356/237; 382/8; 358/106; 65/29; 250/562, 563, 572

[56] References Cited

U.S. PATENT DOCUMENTS

| | | | |
|---|---|---|---|
| 4,021,217 | 5/1977 | Bondybey et al. | 356/430 |
| 4,067,651 | 1/1978 | Watkins | 356/384 |
| 4,168,907 | 9/1979 | Presby | 356/73.1 |
| 4,280,827 | 7/1981 | Murphy et al. | 356/73.1 |
| 4,319,901 | 3/1982 | Pellegrin et al. | 356/73.1 |
| 4,547,895 | 10/1985 | Mita et al. | 382/8 |
| 4,583,851 | 4/1986 | Yataki | 356/73.1 |
| 4,678,327 | 7/1987 | Yoshida et al. | 356/73.1 |
| 4,882,497 | 11/1989 | Inoue et al. | 356/73.1 |
| 4,924,087 | 5/1990 | Bailey et al. | 356/73.1 |
| 4,973,343 | 11/1990 | Frazee, Jr. et al. | 356/384 |
| 5,015,867 | 5/1991 | Siegel et al. | 356/73.1 |

*Primary Examiner*—David K. Moore
*Assistant Examiner*—Barry Stellrecht
*Attorney, Agent, or Firm*—E. E. Leitereg; V. D. Duraiswamy; W. K. Denson-Low

[57] ABSTRACT

Flaws in an optical fiber are automatically classified as to type by obtaining separate camera images of the fiber illuminated at different angles, and analyzing the images to detect the presence of optical patterns that are characteristic of each different type of flaw. Nominal and actual fiber boundaries are preferably first determined, preferably using noncoherent light, and an initial classification made according to the nature of the differential between the two. An analysis under a side light beam can then be performed to distinguish flaws such as splices, hard versus soft external debris, bubbles, internal debris and uncured buffer. The system reverts to a boundary light analysis to characterize a splice once it has been detected. The boundary analysis is preferably performed with a combination of diffused backlighting transmitted through the fiber, and reflected frontlighting at an angle of about 15°–30° to the fiber axis. The focused beam analysis is preferably performed with a laser beam at an angle of about 15°–45° to the fiber axis.

48 Claims, 6 Drawing Sheets

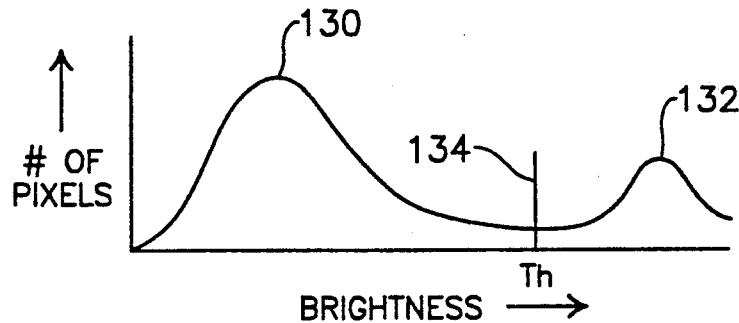
Fig.6a   Fig.6b
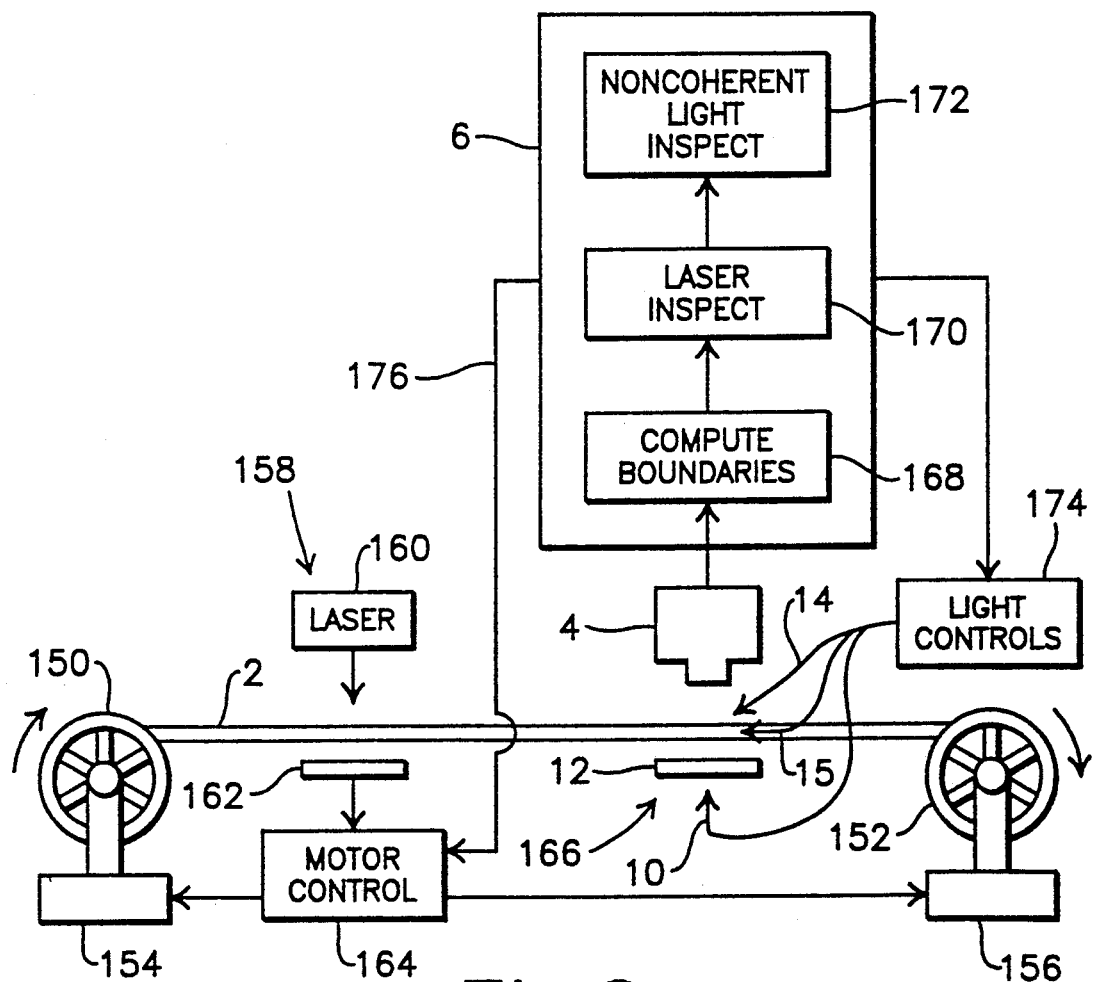
Fig.7
Fig.8

AUTOMATED METHOD OF CLASSIFYING OPTICAL FIBER FLAWS

BACKGROUND OF THE INVENTION

1. Field of the Invention

This invention relates to methods for classifying flaws present in an optical fiber.

2. Description of the Related Art

Optical fibers typically have a glass filament core, consisting of a cladding surrounding a wave guiding core, which in turn is surrounded by a protecting sheath of organic material. Commonly referred to as the "buffer layer", this sheath has been found to have flaws such as debris, bad splices, necks, nicks, bulges, bubbles, uncured portions or other non-uniformities which occur as a result of the fabrication and/or handling of the fiber. The existence of such flaws can become critical for certain fiber optic applications which place significant demands upon the fiber's tensile strength. One such stressful application is in the deployment of fiber during the flight of a fiber optic guided missile. In this situation, the fiber may be stressed at levels approaching its intrinsic strength. Pre-existing defects in the coating may permit mechanical contact with the glass fiber. This can weaken the fiber so that it is likely to break at stresses lower than the mechanical proof stress, which is estimated to be large enough to endure successful fiber payouts.

A detailed inspection of the fiber is thus important to ensure its survivability. This inspection has generally been performed manually with a microscope on the fiber end. However, with missile fiber lengths being on the order of tens of kilometers, manual inspection is inadequate. Furthermore, the inspection may have to be repeated to guarantee a rigorous control of fiber quality after handling and/or shipping.

An automated system for the detection of fiber flaws is disclosed in U.S. Pat. No. 4,924,087, issued May 8, 1990 in the name of Wilbur M. Bailey et al., "Optic Fiber Buffer Defect Detection System", assigned to Hughes Aircraft Company, the assignee of the present invention. In this patent a fiber travels past an inspection station where it is illuminated by one or more laser beams at right angles to the fiber axis. Scattering of the laser beams out of a plane orthogonal to the fiber axis is automatically observed and taken as an indication of a buffer flaw. The fiber can then be stopped and the flaw manually inspected to determine its nature, and whether it requires the flawed section of the fiber to be removed.

The improved system described above still requires a manual inspection step after the presence of a flaw has been detected. This step is both costly and time consuming. Furthermore, during the period the fiber is stopped for manual inspection, the automatic flaw detection system cannot be used for the remainder of the fiber.

SUMMARY OF THE INVENTION

The present invention seeks to provide an automated method for classifying defects in optical fibers and determining their severity, so that this task can be performed more rapidly and with less expense than at present, and with a high degree of accuracy.

These goals are accomplished by automatically determining both the nominal and actual edge of the fiber in the vicinity of a flaw, determining the differential between the nominal and actual fiber boundaries over at least a portion of the flaw, and at least tentatively classifying the flaw based upon said differential. In some cases the classification can be completed based upon the boundary analysis; in others an additional automated focused beam analysis is employed to complete the classification, possibly followed by another boundary analysis.

The boundary analysis is preferably performed by backlighting the fiber with a diffused noncoherent light that is transmitted through the fiber, obtaining a camera image of the flaw area, pixelizing the image, and determining the boundary conditions based upon the pixel brightnesses. The fiber may also be frontlit at an angle of about 15°–30° to the fiber axis while the image is obtained. During subsequent analysis a focused beam, preferably a laser beam, is directed onto the flaw at an angle within the approximate range of 15°–45° to the fiber axis, while its reflectance is observed from a camera angle greater than 60° to the fiber axis (preferably orthogonal), with the focused beam generally orthogonal to the camera line of sight.

To determine whether the flaw is a splice, a focused beam analysis is performed to determine the presence or absence of a pair of spaced surface regions on the fiber that are generally orthogonal to the fiber axis and differ from the remainder of the fiber surface; this analysis is enhanced by processing the image through a Laplacian filter. When a splice has been detected, its nature is determined by a backlighted boundary analysis. A nick can be distinguished from a neck in the fiber, and a bulge can be distinguished from debris on the fiber surface, by determining whether the flaw is present on opposite sides of the fiber and/or determining the second derivative of the actual/nominal boundary differential with respect to distance along the fiber axis. A higher second derivative indicates a nick or debris, while a lower value indicates a neck or a bulge. Different kinds of debris can be distinguished from each other by the brightness of reflection during laser analysis. Debris can be distinguished from bubbles by counting transitions between light and dark areas during focused beam analysis, with a higher number of transitions indicating bubbles. Bubbles in turn can be distinguished from an uncured buffer with focused beam analysis by observing the distribution of bright spots within the fiber, with distributed spots indicating bubbles and localized spots uncured buffer. For each of the last two analyses a pixelized image of the laser illuminated fiber is enhanced with a Laplacian filter, and then binarized to dark and light pixels based upon the brightness of each pixel relative to a threshold brightness level. Internal debris can be distinguished from uncured buffer by the brightness of spots observed during focused beam analysis.

The automated flaw classification method can be combined with an automated flaw detection method, such as that disclosed in U.S. Pat. No. 4,924,087, to provide a completely automated process. When a flaw is detected at a first inspection station, the fiber is automatically advanced to a second station at which the classification analysis is performed.

These and other features and advantages of the invention will be apparent to those skilled in the art from the following detailed description, taken together with the accompanying drawings, in which:

DESCRIPTION OF THE DRAWINGS

FIG. 6a and 6b are number tables illustrating the operation of Laplacian filters used by the invention to enhance overall and vertical image features respectively;

FIG. 7 is a graph illustrating a brightness thresholding operation employed by the invention; and FIG. 8 is a block diagram showing an automated fiber optic flaw classification system coordinated with an automated flaw detection system.

DETAILED DESCRIPTION OF THE INVENTION

Figure 1:
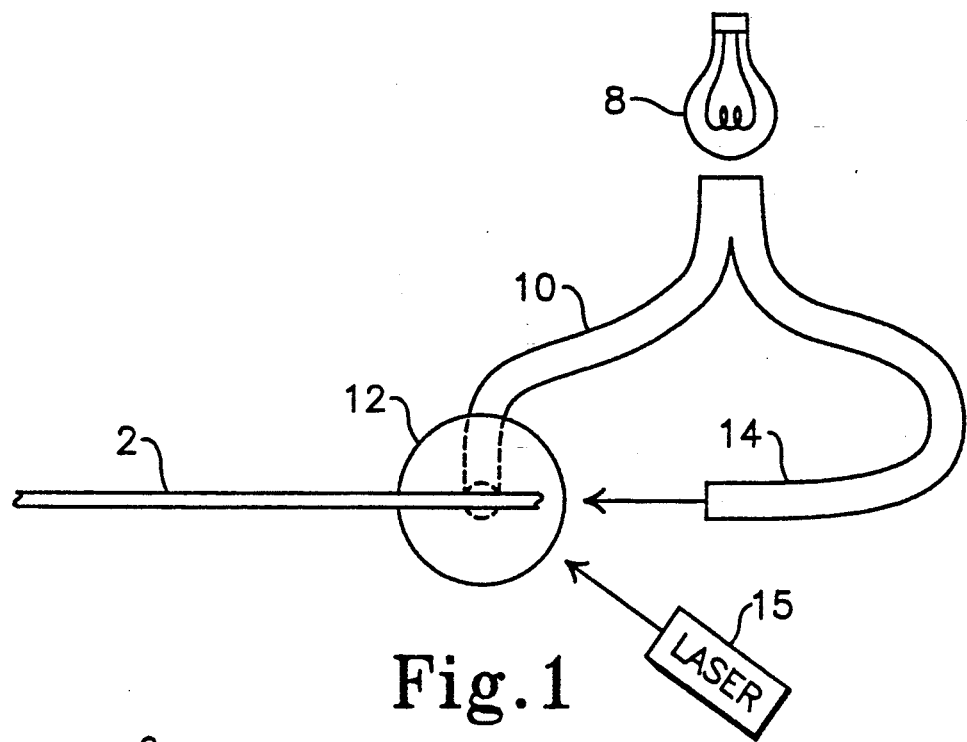
FIG. 1 is a simplified plan view of a system for implementing automatic flaw classification for an optical fiber in accordance with the invention.
Figure 2:
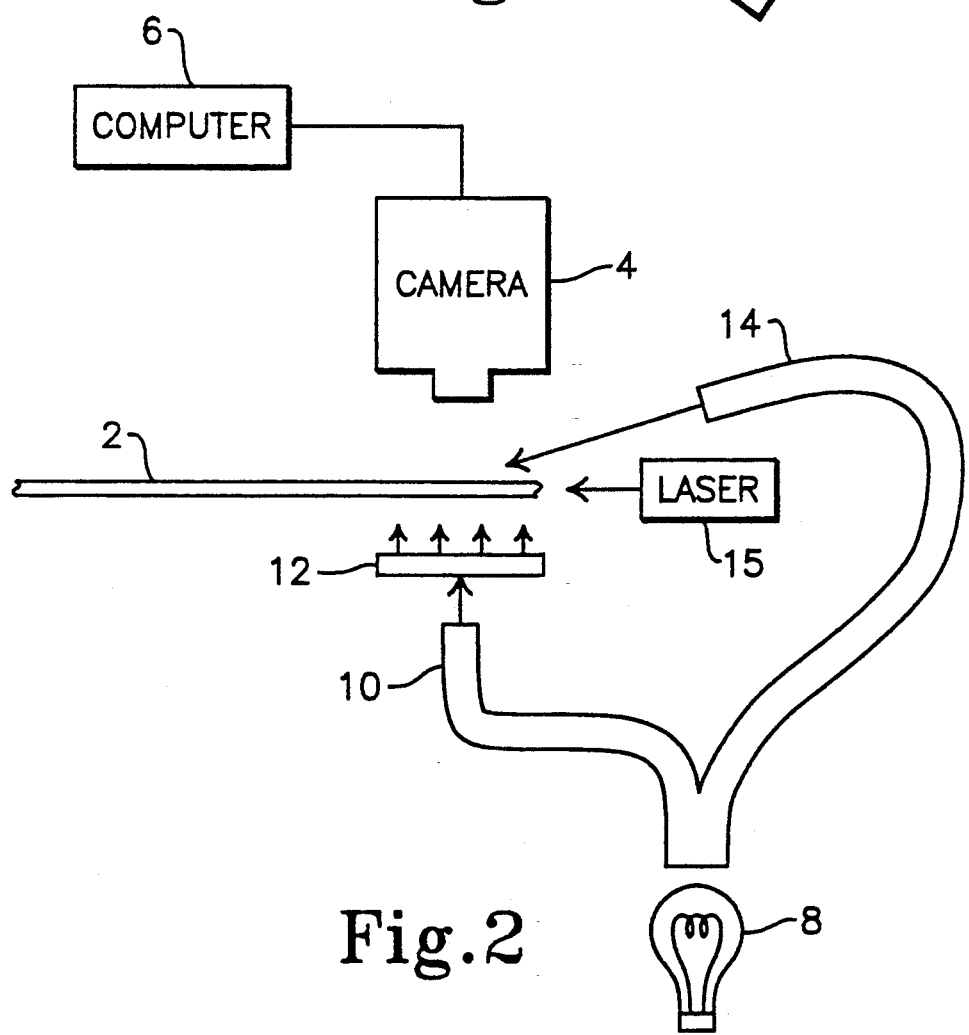
FIG. 2 is a front elevational view of the system of FIG. 1.

FIGS. 1 and 2 illustrate a system for implementing the invention to automatically classify flaws that have been located in an optical fiber. Although variations in the sequence of steps are possible, the system will generally first perform a backlit boundary analysis of the fiber, then a further analysis under an angled focused beam, with a possible final backlight analysis.

An optical fiber 2 travels axially below a camera 4 (shown only in FIG. 2), which obtains one or more images of the fiber in the vicinity of a detected flaw. The camera image is provided to a computer 6 that performs the analysis. The optical fiber 2 is held stationery under the camera while the images are taken, and is then advanced until another defect comes within the camera's sight. The camera's line of sight is at least 60°, and preferably about 90° to the fiber axis.

A backlight on the opposite side of the fiber from the camera is provided, preferably by a noncoherent light source 8 such as a 150 watt bulb, via an optical fiber 10. The opposite end of fiber 10 from bulb 8 illuminates a diffuser 12 which is placed on the opposite side of fiber 2 from the camera 4. Without the diffuser, the backlight fiber 10 would have to be directed at a considerable angle to the camera axis, rather than directly along the camera axis, to avoid blinding the camera; this would degrade the contrast of the image captured by the camera. While a laser light source could be used instead of a noncoherent source, this would aggravate the potential of blinding the camera.

A second light source is provided by another optical fiber 14 that is also illuminated by bulb 8, or that alternately can have its own light source. The light emitting end of fiber 14 is located on the same side of the fiber 2 as the camera 4, but is directed onto the flawed area of the fiber 2 at a relatively shallow angle of about 15°–30° preferably about 22° ) to the fiber axis. At this angle portions of the beam may be reflected back to the camera from a flaw. While the system could operate with the backlight provided by fiber 10 alone, the addition of an angled frontlight from fiber 14 improves the image contrast when both light sources are on simultaneously. If the second noncoherent light source 14 is used, however, it is important that it be held within the described angular range to the axis of fiber 2. Otherwise, incorrect information on the fiber flaw being analyzed may result. A laser source could also be used for the frontlight, but again noncoherent light is preferred for this purpose. Suitable optical fibers for the back and frontlights are provided by Dolan Jenner, Inc., which emit noncoherent beams about 1 cm in diameter.

A laser 15, such as a Class 3B, 5mW HeNe device, is positioned to illuminate the fiber from an angle of about 15°–45° (preferably about 28°) to the fiber axis, and generally orthogonal to the line of sight of camera 4. A non-coherent light source could be used instead of a laser if it were focused (a focused beam is defined as including a collimated beam), but its power would be on the order of about 100–150 W as opposed to the preferred 3–5 mW laser source. Laser illumination is generally done separately from illumination with the back and frontlights, but in certain cases it may be desirable to combine them. The laser beam is typically about 3 mm in diameter, as compared to a typical fiber diameter of about 250 microns.

Figure 3A:
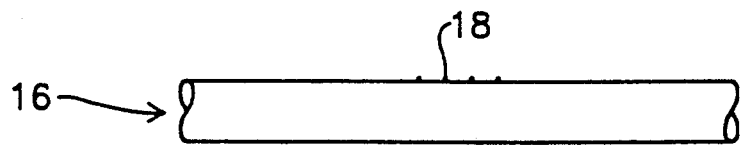
FIGS. 3a–3j are illustrative drawings of various types of fiber optic flaws that can be automatically classified with the invention.

Various types of flaws that may be automatically classified with the invention are illustrated in FIGS. 3a–3j. All of the flaws are shown in relation to a standard optical fiber 16. The illustrated flaws are:

FIG. 3a: External particles or debris 18 are shown on the fiber surface. Debris may also be located internally within the boundaries of the fiber.

Figure 3B:

FIG. 3b: A gradual circumferential narrowing of the fiber diameter, followed by a gradual expansion back to its nominal diameter, is referred to as a neck 20.

Figure 3C:

FIG. 3c: A gradual circumferential increase in the fiber diameter, followed by a gradual reduction back to the nominal diameter, is referred to as a bulge 22.

Figure 3D:
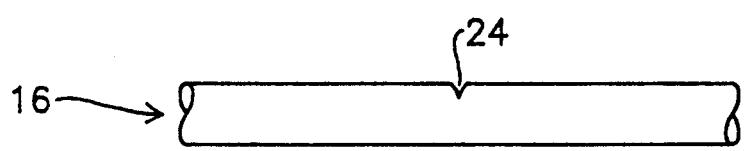

FIG. 3d: A nick 24 is a sharp intrusion into the fiber's outer surface on one side.

Various types of splices are also possible. The circumference of the fiber should ideally remain constant from the fiber on one side of the splice, all the way through the splice to the fiber on the other side. A splice is typically characterized by a pair of vertical bands extending around the circumference of the fiber at opposite ends of the splice.

Figure 3E:
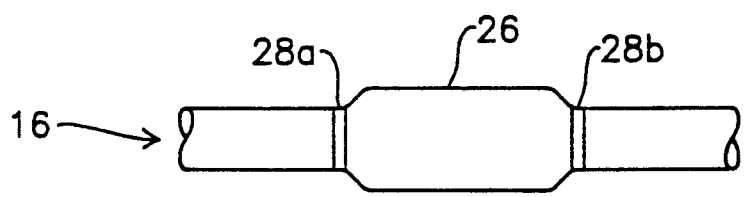

FIG. 3e: A splice 26 that bulges outward is illustrated. The characteristic bands orthogonal to the fiber axis are indicated by reference numbers 28a and 28b.

Figure 3F:
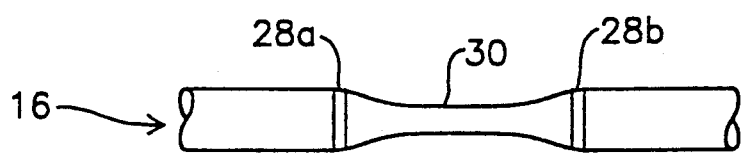

FIG. 3f: A splice is illustrated which forms a neck 30.

Figure 3G:
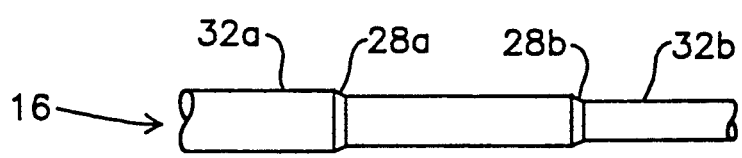

FIG. 3g: In this illustration two sections of fiber 32a and 32b of different diameters have been spliced together. The flaw lies not in the splice itself, but in the selection of optical fibers that have been joined together by the splice.

Figure 3H:
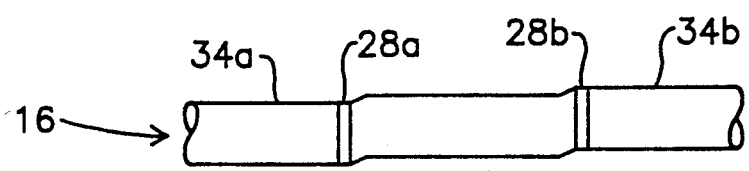

FIG. 3h: The two fiber sections 34a, 34b that are spliced together may be misaligned or offset from each other, as illustrated in this figure.

Figure 3I:

FIG. 3i: A good splice, whose section is of equal diameter to the fiber sections on either side and coaxial therewith, is illustrated.

Figures 3J, 4A:
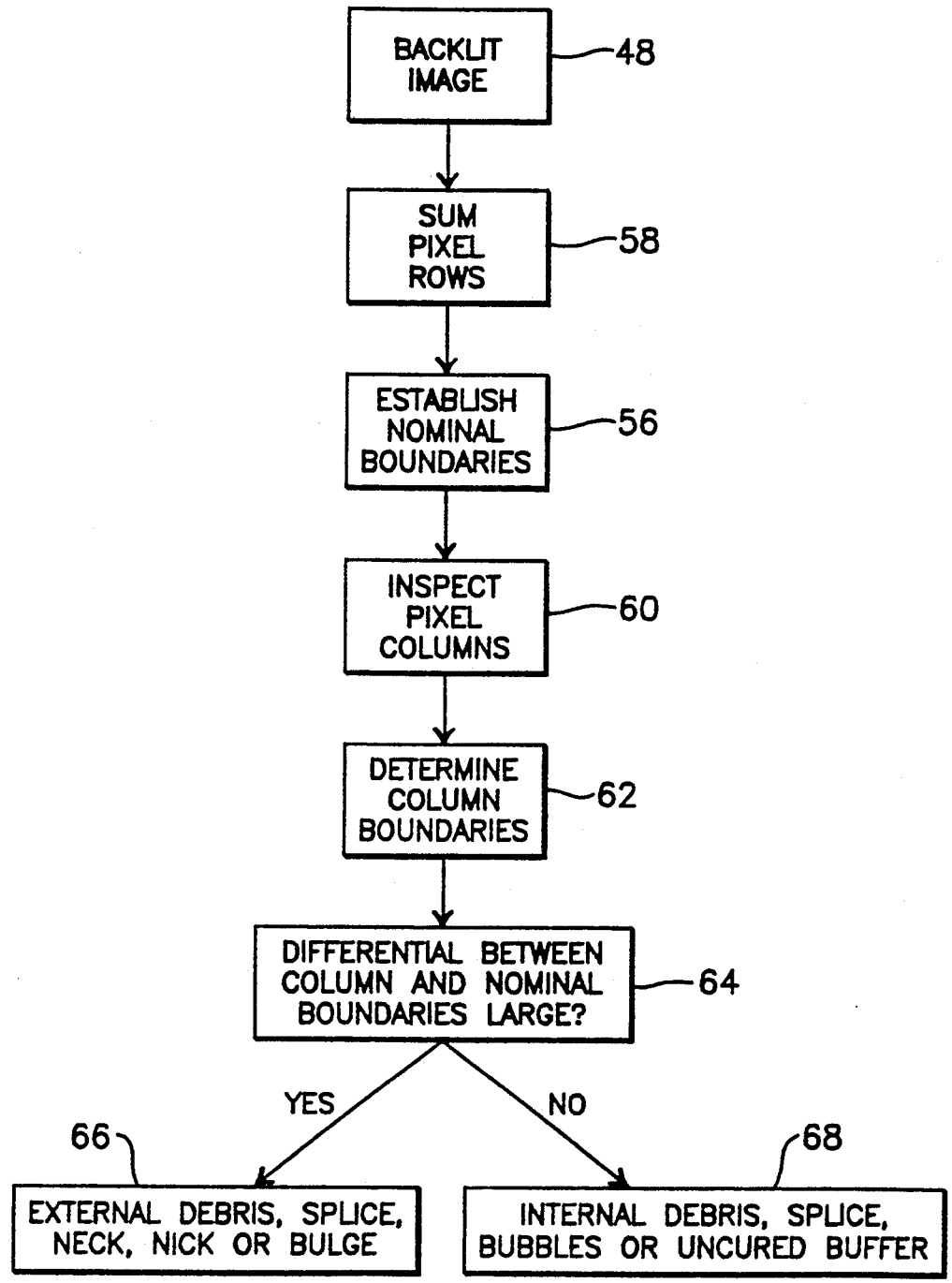
FIGS. 4a, 4b, and 4c are flow diagrams of a classification routine that implements the invention.

FIG. 3j: An enlarged cross-section of an optical fiber is illustrated. The fiber typically has an inner glass core 38, an outer glass core 40, an inner buffer layer 42, and an outer buffer layer 44. Air bubbles 46 may be introduced between the inner and outer buffer layers during fabrication without deforming the fiber surface. The bubbles are generally distributed through the interface of the inner and outer buffer layers.

Other flaws in the fiber may also be encountered, such as a section of the fiber in which the buffer layer is uncured, the fiber surface is scuffed or scraped, or the outer buffer layer parallel to the fiber axis is split. Classification of the flaw is important because it determines the remedial action, if any, that should be taken. For example, some types of debris can often simply be rubbed off, whereas other types of debris may require replacement of the defective fiber section. Also, the automatic flaw detection system of U.S. Pat. No. 4,924,087 will detect both good and bad splices; good splices can be left intact, while bad slices can be replaced depending upon their severity. For purposes of the present invention, it is assumed that there will be a single predominant defect within the camera's field of view.

The flaw classification is implemented with two complementary camera images of the fiber taken in the vicinity of the flaw. In the first image the fiber is backlit, preferably with noncoherent light, and also preferably with the oblique noncoherent frontlight described above. In the second image the fiber is illuminated obliquely from the side, preferably with laser light. The various defects are characterized by their typical appearances in the two images. Additional cameras could also be used at various angles to the first camera, with corresponding additional light sources provided. For example, a second set of light sources and camera could be provided at a 90° rotation about the fiber axis to the first set described above. Due to the modular system design, the system can be easily augmented to incorporate additional defects as they appear.

Figure 5:
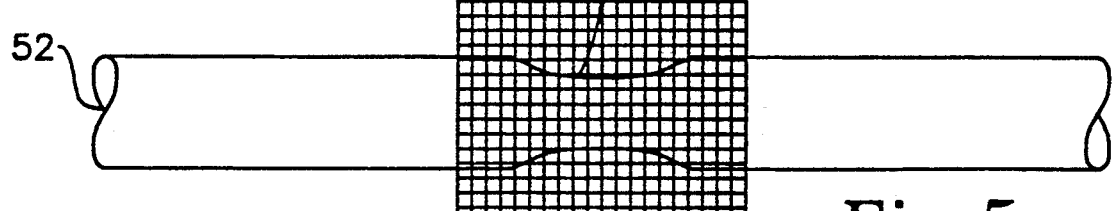
FIG. 5 is an illustration of the pixelization analysis used in the preferred embodiment of the invention.

A flow diagram outlining the initial steps in a typical analysis is provided in FIG. 4a. While other sequences may be performed, the approach illustrated herein appears at present to be the most efficient. In the first step (block 48), a backlit camera image of the fiber flaw is obtained. This image may be enhanced by simultaneously frontlighting the flaw area, as described. The image is then pixelized within the computer 6 by segmenting it into an array of pixels, the brightness of each of which can then be separately evaluated. A typical pixelization scheme is illustrated in FIG. 5. The pixel array 50 is shown superimposed over a section of fiber 52 that includes the flaw, in this case a neck 54. The pixel array is typically about twice the nominal fiber diameter in width, and extends for approximately 0.5–1 mm parallel to the fiber axis. A 512×512 pixel array would be typical.

Using the pixelized image, nominal boundary edges for the fiber are established (block 56 in FIG. 4a). This can be accomplished by summing the pixel gray scale brightnesses on a row-by-row basis (block 58). The fiber edges will appear as considerably darkened bands parallel to the fiber axis in the backlit/frontlit image. Thus, the two pixel rows which exhibit darkness peaks will correspond to the location of the nominal fiber edges on either side of the flaw. Alternately, but perhaps less accurately, the nominal fiber boundaries could simply be pre-programmed as determined by the fiber specifications.

In the next step of the analysis, the pixel columns in the camera image are individually evaluated by the computer (block 60) to locate the upper and lower fiber boundaries on a column-by-column basis (block 62). The actual fiber boundaries, and their variance from column to column, correspond to the darkened pixels within each column. The actual column-by-column edge locations can thus be obtained and compared in the computer with the nominal fiber edges, and the differential between the two computed using a conventional boundary computation algorithm to determine fiber boundaries. An initial classification of the flaw is then made depending upon whether the computed differential is large or small (block 64).

If the computed differential is large, the flaw can generally be categorized as external debris, a splice, a neck, a nick or a bulge (block 66). If the differential is small, the presence of internal debris, a splice, bubbles or a section of uncured buffer is indicated (block 68). The magnitude of the differential is not determinative of whether a splice is present, since different types of splices can produce either large or small differentials; the identification of a splice is accomplished with the laser analysis described below.

Whether a differential between the actual and nominal fiber boundaries may be categorized as "large" or not is determined empirically. By taking a relatively large number of flawed fibers and comparing the calculated boundary differentials with the type of flaw as determined by manual inspection, a data base may be established from which a threshold level distinguishing "large" from "small" differentials for a particular system can be obtained. A similar empirical approach may be used to determine a dividing line between "high" and "low" values of second derivative in distinguishing between a nick and a neck, as discussed below.

Figure 4B:
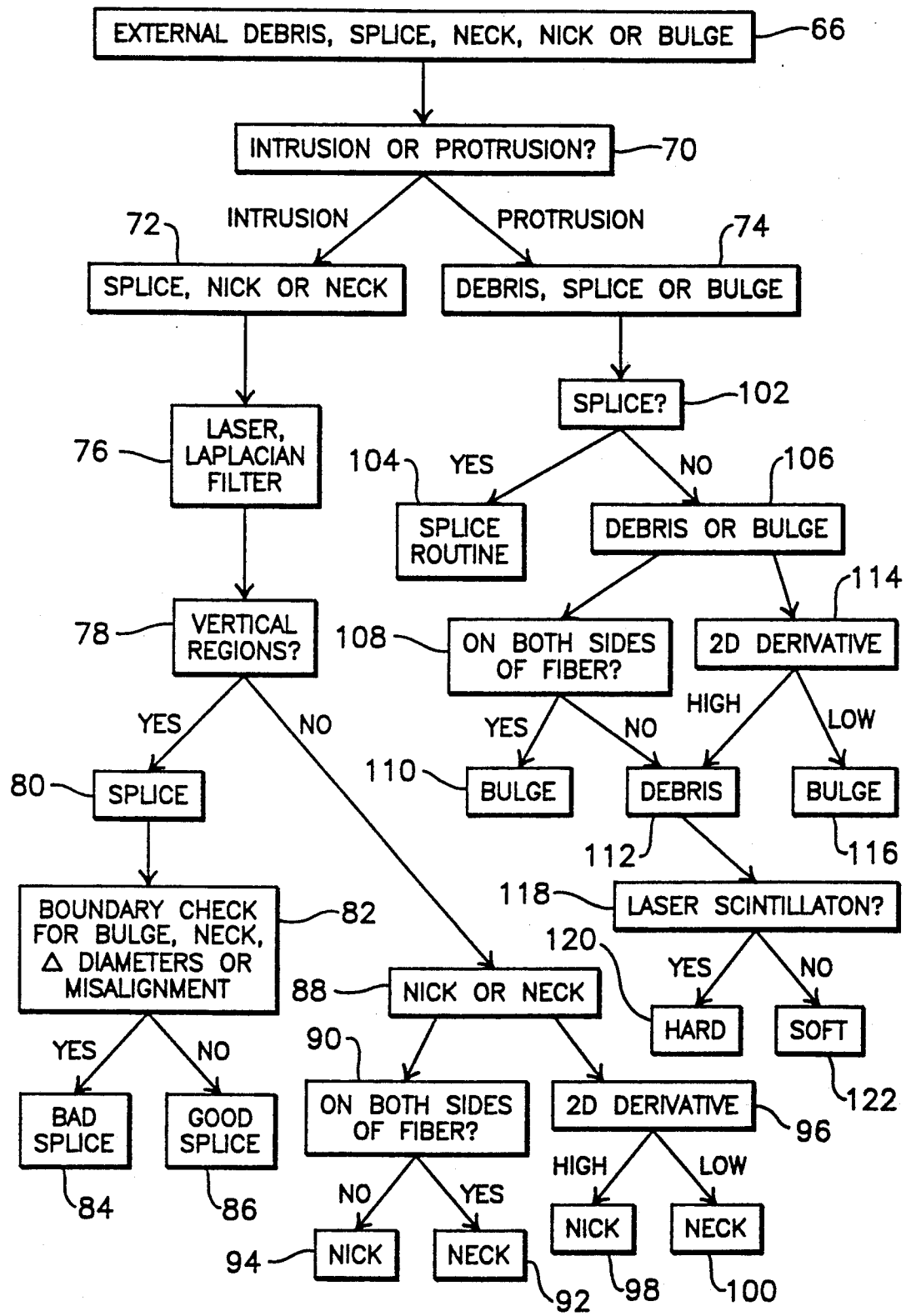

A flow chart is presented in FIG. 4b for further analysis of the flaw when the differential between the actual and nominal fiber boundaries has been determined to be large. In this event, the flaw is first characterized as an intrusion into or a protrusion out from the fiber by determining the sign of the first derivative of the differential with respect to distance parallel to the fiber axis (block 70). An intrusion will indicate a splice, nick or neck (block 72), while a protrusion will indicate external debris, a splice or a bulge (block 74); a splice may have either intrusion or protrusion characteristics, or both.

To determine whether an intrusion is the result of a splice, the fiber is illuminated with the laser beam (block 76) and the image is analyzed by the computer to determine the presence or absence of the pair of spaced darkened vertical regions 28a and 28b which accompany a splice (block 78). To enhance the contrast of these vertical features relative to the remainder of the fiber, the computer is preferably programmed to perform an initial Laplacian filter routine that emphasizes vertical features. A Laplacian filter is an image enhancement technique that improves the contrast for desired geometric features. To enhance the overall image contrast, a Laplacian filter matrix such as that illustrated in FIG. 6a would be used. The illustrated filter is a 3×3 pixel matrix, which is superimposed over a section of the pixel matrix 50 established for the camera image on a pixel-to-pixel basis. Thus, the 3×3 filter will overlap a 3×3 pixel section of the matrix 50. The brightness level of each overlapped pixel within matrix 50 is amplified by the magnitudes given for the various pixel locations in FIG. 6a; the particular magnification factors are merely illustrative, and can be considerably varied. However, for a uniform contrast enhancement, the magnification pattern should be symmetrical within the filter matrix. The filter matrix is then shifted to successive adjacent sections within the pixel matrix 50, with the contrast enhancement performed at each different location, until the entire matrix 50 has been covered.

To enhance only vertical features within the pixel matrix 50, a filter such as that shown in FIG. 6b would be used. With this filter, the light values of bright vertical features will be increased relative to the surrounding pixels, while the values of dark vertical features will be reduced, thus enhancing the contrast of vertical objects. When this filter has been applied over the entire area of the pixel matrix 50 by moving it in succession from one section of the matrix to the next, the contrast between vertical features in the image and the background is significantly increased. In this way the presence or absence of the characteristic vertical regions associated with a splice can be better determined.

If a determination is made that the flaw is a splice (block 80), the computer is programmed to automatically revert the system back to a boundary determination mode such as that illustrated in FIG. 4a, in which the fiber is backlit (and preferably also frontlit) with noncoherent light as described above, and the differential between the actual and nominal fiber boundaries is determined (block 82). From this second boundary check it can be determined whether the splice has a bulge (FIG. 3e), a neck (FIG. 3f), a differential in the diameters of the fiber sections that are joined by the splice (FIG. 3g), or a misalignment between the sections joined by the splice (FIG. 3h). If any of these conditions exist (block 84), a decision can be made as to whether the severity of the flaw calls for the splice to be replaced. If, on the other hand, the boundary check reveals a continuous diameter from the fiber on one side of the splice through the splice and to the fiber on the other side, then a good splice is indicated (block 86) and no remedial action is necessary.

If a pair of vertical regions on the surface of the fiber is not revealed by the laser analysis, then the flaw can be identified as a neck or a nick (block 88). Two different analyses may be performed to distinguish between these flaws. In one, the fiber boundaries (as determined from the backlit/frontlit image) are evaluated by the computer to determine whether the intrusion is present on both sides of the fiber (block 90); a positive response indicates a neck (block 92), while a negative response indicates a nick (block 94).

The second method of distinguishing a nick from a neck involves a calculation of the intrusion's second derivative with respect to distance parallel to the fiber axis; this calculation is again performed by the computer based upon the pixelized backlit image (block 96). It has been observed that the second derivative for a nick is substantially higher than for a neck. A high value of calculated second derivative may thus be taken to indicate that the flaw is a nick (block 98), while a low value indicates that it is a neck (block 100). The threshold level distinguishing a "high" from a "low" value of second derivative is determined empirically, as outlined above.

Now assume that the backlit analysis with noncoherent light reveals that the flaw is a protrusion that can be either external debris, a splice or a bulge (block 74), rather than an intrusion. In this case, an analysis is again performed under laser light to determine whether the flaw is a splice (block 102). As with an intrusion, an inspection is made for a pair of spaced vertical regions (blocks 76, 78). If such vertical regions are found, the same splice routine (block 104) as for an intrusion is entered to determine the nature of the splice (blocks 80–86).

If no splice is indicated, then the protrusion can be characterized as either debris or a bulge (block 106). To distinguish between these two types of flaws, two routines similar to those used to distinguish between a nick and a neck are available; these routines are performed on the image obtained from the backlight (and preferably also the frontlight). The presence of a protrusion on both sides of the fiber (block 108) indicates a bulge (block 110), while a protrusion on only one side of the fiber indicates debris (block 112). A high value of the second derivative of the protrusion with respect to distance parallel to the fiber axis (block 114) indicates debris (block 112), while a low value indicates a bulge (block 116). If either or both of these analyses are performed and result in a finding that the flaw consists of debris, a further analysis can be made under laser illumination to determine types of debris. This analysis involves illuminating the fiber with the laser beam, and analyzing the resulting camera image. If spots on the image corresponding to the debris scintillate and appear very bright under the laser (block 118), a harder type of debris is indicated (block 120). If, on the other hand, the debris does not appear under the laser beam, a softer type of particle is indicated (block 122). The type of debris may be further characterized in this manner to distinguish between candidates such as imbedded dirt, carbonaceous surface materials, lint, etc. Since there may still be internal debris, the fiber is further analyzed as described below.

Figure 4C:
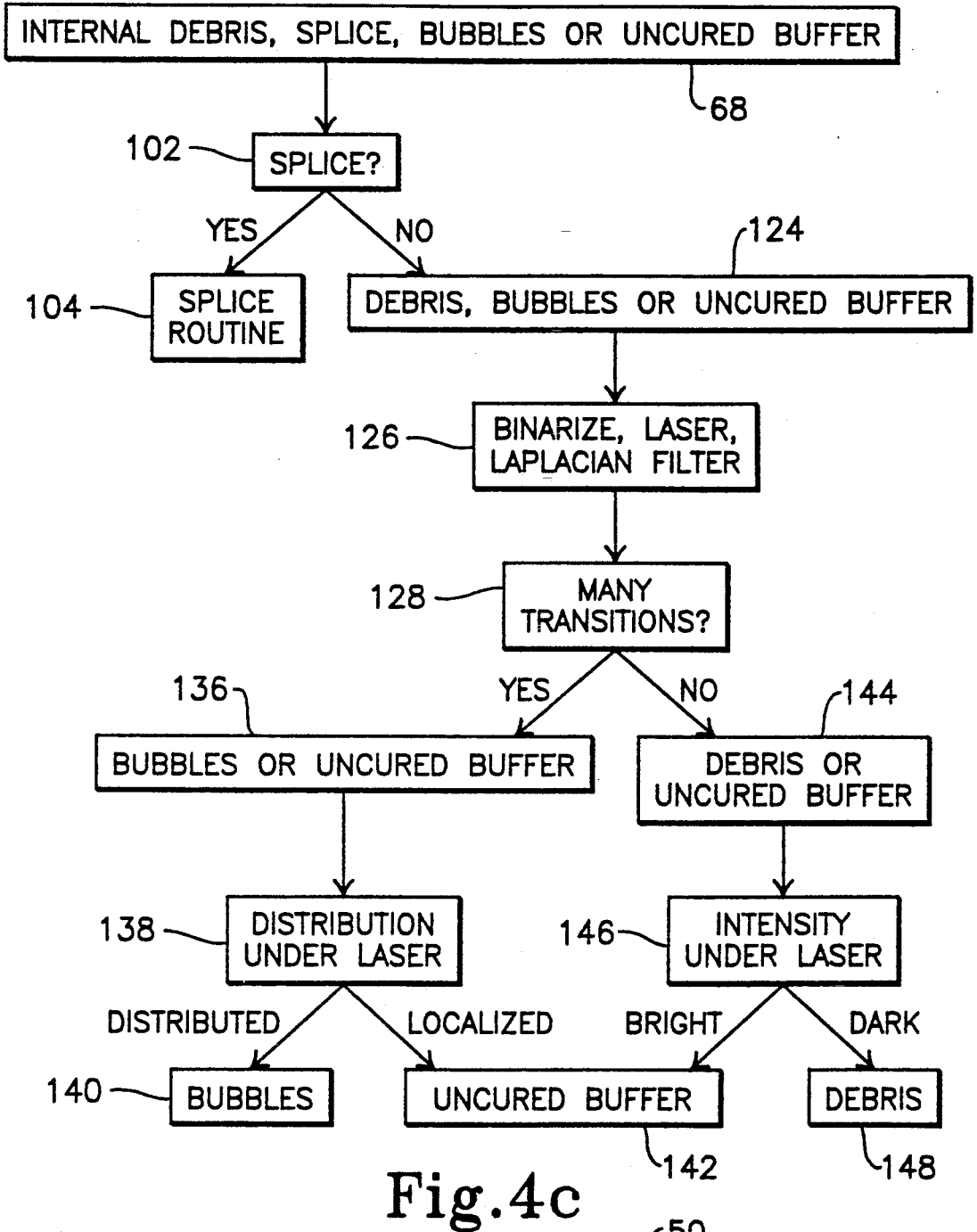

Now consider the case in which the initial boundary differential analysis indicates that the flaw consists of either internal debris, a splice, bubbles or a section of uncured buffer (block 68). A flow chart for subsequent analysis is given in FIG. 4c. A determination is first made as to whether the flaw is a splice (block 102). If a splice is indicated, the same splice routine (blocks 80–86, 104) is performed as discussed above to characterize the nature of the splice. If the splice test is negative, then the flaw can be characterized as either internal debris, bubbles or uncured buffer (block 124). The next step in the particular sequence illustrated in FIG. 4c is to effectively count the number of bright spots which appear in the fiber under laser illumination. A large number of bright spots is consistent with the presence of bubbles, while a small number is consistent with internal debris; uncured buffer may present either a large or a small number of bright spots. To perform the count, the laser illuminated image is binarized into fully black and white levels of intensity, with no gray scale areas in between. This is accomplished by determining whether the brightness of each pixel within the image lies above or below a threshold level, with those pixels above the threshold being deemed to be white and the remaining pixels black. To enhance the overall image contrast prior to binarization, the laser illuminated fiber image is preferably first processed through a Laplacian filter such as that illustrated in FIG. 6a in the computer. The result of the Laplacian filter and binarization process (block 126) is a pixel matrix in which some of the pixels are white (corresponding to bright spots in the image) and the remainder are black.

To count the bright spots, individual parallel rows of pixels are analyzed with the computer to count the number of transitions from black to white and from white to black along each row; each pair transitions corresponds to a bright spot. A large number of pixel rows, perhaps on the order of 100, are analyzed in this manner to provide an indication of the number of transitions (bright spots) within the fiber (block 128).

To make the initial determination of a threshold level for distinguishing "bright" pixels from the other pixels prior to binarization, a histogram relating gray scale brightness to the number of pixels at each brightness level can be computer generated. An illustrative histogram is illustrated in FIG. 7. When bright spots are present, the histogram will typically have two peaks, one at a background brightness level 130, and the other at a higher brightness level 132. The threshold level 134 for distinguishing a bright pixel from the background is assigned to a brightness level between the two peaks which is occupied by few or no pixels; this threshold level can simply be the average of the two peak levels.

If a large number of transitions are present, the presence of either bubbles or uncured buffer (block 136) is indicated. These two flaws can be distinguished from each other by analyzing the spatial distribution of the bright spots under laser illumination (block 138). The same laser image that was used to determine the number of transitions may be employed for this purpose also. If the bright spots are well distributed throughout the outer buffer layer in a regular arrangement of many small regions, the presence of bubbles is indicated (block 140); a more localized distribution of bright spots, typically a large vertical blob with similar regions on either side, indicates uncured buffer (block 142).

To distinguish internal debris from uncured buffer (block 144), a camera image of the fiber in the vicinity of the flaw is again obtained under laser illumination. This image is evaluated by the computer to determine whether the spots corresponding to the recognized transitions are bright or dark (block 146). If they are bright, uncured buffer is indicated (block 42). If they are darker than the background, internal debris is indicated (block 148).

Many different types of fiber flaws can thus be very rapidly recognized and characterized. The computer can be programmed to distinguish between additional types of flaws as desired. For example, a scuff would be characterized by several elongated, vertical, medium intensity regions, while a split in the outer buffer layer could be characterized by a well-defined horizontal region that extends over a substantial portion of the camera image. The automated system offers a substantial improvement over the prior manual inspection procedure.

A system for both detecting and characterizing optical fiber flaws is shown in block diagram form in FIG. 8. The optical fiber 2 moves between a payout reel 150 and a takeup up reel 152 which are rotated by motors 154 and 156, respectively. Defects in the fiber are detected, but not characterized, at a first inspection station 158. This station preferably uses an automated flaw detection system such as that disclosed in U.S. Pat. No. 4,924,087. A laser 160 directs a beam orthogonally onto the fiber from one side, while the laser pattern at a detector 162 on the opposite side of the fiber indicates the presence or absence of a flaw. When a flaw is detected, a signal is transmitted to a motor control 164 that causes the fiber to stop when the flaw has reached a second inspection station 166. The automatic flaw classification which is the subject of this invention is performed at this second station. There the fiber is first backlit (and preferably also frontlit) with noncoherent light, and an image thereof is transmitted from the camera 4 to computer 6 for computation of the fiber boundaries (block 168). The computer enters a laser inspection mode (block 170) and a subsequent noncoherent light inspection mode (block 172) as required, and as described above, to complete the characterization of the flaw. Signals are transmitted from the computer to controls 174 for the noncoherent and laser light sources. When the automated flaw classification process has been completed, either the flaw is cut out and the two ends of the fiber spliced together, or the fiber travel is resumed if the flaw does not merit removal. In the latter event, the computer transmits a signal over line 176 to the motor controller 164 to initiate a resumption of the reel rotation.

While illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. An automated method for classifying a flaw in an optical fiber, comprising:
   determining the nominal boundary of the fiber in the vicinity of the flaw,
   determining the actual boundary of the fiber in the vicinity of the flaw,
   determining the differential between the nominal and actual fiber boundaries over at least a portion of the flaw, and
   classifying said flaw as to a type of flaw based upon said differential
   wherein said nominal boundary, actual boundary, and differential determinations are made by obtaining a backlit image of the fiber in the vicinity of the flaw, pixelizing said image, and making said determinations based upon the gray scale values of said pixelized image.

2. The method of claim 1, wherein back light illumination for said fiber is processed through an optical diffuser before illuminating the fiber.

3. The method of claim 1, wherein said fiber is frontlit with light in the vicinity of the flaw simultaneously with said backlighting, said frontlighting being directed at an angle within the approximate range of 15°-30° to the fiber axis, and its reflectance is observed from an angle approximately orthogonal to the fiber axis.

4. The method of claim 3, wherein said frontlight angle, observation angle and fiber are approximately coplanar.

5. The method of claim 1, wherein light is transmitted through said fiber from a first angle, an image of said transmitted light is obtained, and said nominal boundary, actual boundary and differential determinations are made based upon said image.

6. The method of claim 5, wherein light from a second angle is reflected off said fiber, said image including both the transmitted and the reflected light.

7. The method of claim 1, wherein said flaw is further classified by illuminating it with a focused light beam, and observing the focused beam reflectance pattern from the vicinity of the flaw.

8. The method of claim 7, wherein the focused beam is directed onto the flaw at an angle within the approximate range of 15°-45° to the fiber axis, and its reflectance is observed from an angle greater than 60° to the fiber axis.

9. The method of claim 8, wherein said focused beam and fiber are approximately coplanar in a first plane, said observation angle and fiber are approximately coplanar in a second plane, and said first and second planes are approximately orthogonal.

10. The method of claim 7, wherein said focused beam comprises a laser beam.

11. The method of claim 1, further comprising the step of determining whether the flaw is a splice by observing the presence or absence of a pair of spaced surface regions on the fiber that are generally orthogonal to the fiber axis and differ from the remainder of the fiber surface.

12. The method of claim 11, wherein said observation is made by illuminating the fiber with a focused beam and observing the reflection of said focused beam in the vicinity of the flaw.

13. The method of claim 12, wherein the focused beam is directed onto the flaw at an angle within the approximate range of 15°-45° to the fiber axis, and its reflectance is observed from an angle greater than 60° to the fiber axis.

14. The method of claim 12, wherein an image of the focused beam reflectance from the fiber in the vicinity of the flaw is obtained and vertical regions therein are enhanced by processing the image through a Laplacian filter.

15. The method of claim 12, wherein after the presence of a splice is detected the nature of the splice is detected by backlighting the fiber in the vicinity of the splice, and determining the boundaries of the splice from a backlighted image thereof.

16. The method of claim 1, for a differential indicating that the flaw is an intrusion into the fiber, wherein a nick is distinguished from a neck in the fiber by determining whether the intrusion is present on opposite sides of the fiber.

17. The method of claim 1, for a differential indicating that the flaw is an intrusion into the fiber, wherein a nick is distinguished from a neck in the fiber by determining the second derivative of said differential with respect to distance along the fiber axis, with a higher second derivative indicating a nick and a lower second derivative neck.

18. The method of claim 1, for a differential indicating that the flaw is a protrusion from the fiber, wherein a bulge in the fiber is distinguished from debris on the fiber by determining whether the protrusion is present on opposite sides of the fiber.

19. The method of claim 1, for a differential indicating that the flaw is a protrusion from the fiber, wherein a bulge in the fiber is distinguished from debris on the fiber by determining the second derivative of said differential with respect to distance along the fiber axis, with a higher second derivative indicating debris and a lower second derivative a bulge.

20. The method of claim 1, for a differential indicating that the flaw is debris on the fiber, wherein different types of debris are distinguished from each other by illuminating the fiber in the vicinity of the debris with a focused beam and observing the brightness of the focused light reflected therefrom.

21. The method of claim 1, for a differential indicating that the flaw may be either debris or bubbles within the fiber, wherein debris is distinguished from bubbles by illuminating the fiber in the vicinity of the flaw with a focused beam, observing transitions between light areas and dark areas in the reflected focused beam light along a plurality of traces generally parallel to the fiber axis, and distinguishing between debris and bubbles based upon the number of said transitions, with a higher number of transitions indicating bubbles.

22. The method of claim 21, wherein a pixelized image of focused beam illuminated fiber is obtained, said image is binarized into dark and light pixels based upon the brightness of each pixel relative to a threshold brightness level, and said observation of transitions is performed on said binarized image.

23. The method of claim 22, wherein brightness contrasts within said pixelized image are enhanced by processing the image through a Laplacian filter prior to binarizing the image.

24. The method of claim 1, for a fiber having a core surrounded by a buffer and a flaw that has been classified as either bubbles or uncured buffer within the fiber, wherein bubbles are distinguished from uncured buffer by illuminating the flaw with a focused light beam, observing bright spots in the focused beam light reflected from the flaw, and distinguishing between bubbles and uncured buffer based upon whether the bright spots are distributed through or localized within the fiber, with distributed spots indicating bubbles and localized spots uncured buffer.

25. The method of claim 1, for a fiber having a core surrounded by a buffer and a flaw that has been classified as either debris or uncured buffer within the fiber, wherein debris is distinguished from uncured buffer by illuminating the fiber with a focused light beam, observing spots in the focused beam light reflected from the flaw, and distinguishing between debris and uncured buffer based upon whether the spots are dark or bright respectively.

26. An automated method for classifying a flaw in an optical fiber, comprising:
  determining nominal and actual boundaries of the fiber in the vicinity of the flaw comprising the steps of:
    generating a backlight for the fiber in the vicinity of the flaw,
    obtaining a camera image of the fiber in the vicinity of the flaw against said backlight, and
    pixelizing said image;
  generating differentials between spatial characteristics of said boundaries in said pixelized image along a path generally parallel to the fiber axis; and
  classifying said flaw as to type based upon said differentials.

27. The method of claim 26, wherein said fiber is frontlit with light in the vicinity of the flaw simultaneously with said backlighting, said frontlighting being directed at an angle within the approximate range of 15°-30° to the fiber axis, and its reflectance is observed from an angle approximately orthogonal to the fiber axis.

28. The method of claim 27, wherein said frontlight angle, observation angle and fiber are approximately coplanar.

29. The method of claim 26 wherein said flaw is further classified by illuminating it with a focused light beam, obtaining a camera image of the focused beam reflectance from the fiber in the vicinity of the flaw, and further classifying said flaw based upon the reflectance pattern in said focused beam camera image.

30. The method of claim 29, wherein the focused beam is directed onto the flaw at an angle within the approximate range of 15°-45° to the fiber axis, and said focused beam camera image is taken along a sight line greater than 60° the fiber axis.

31. The method of claim 30, wherein said focused beam and fiber are approximately coplanar in a first plane, said camera sight line and fiber are approximately coplanar in a second plane, and said first and second planes are approximately orthogonal.

32. The method of claim 29, wherein said focused light beam comprises a laser beam.

33. An automated method for detecting and classifying a flaw in an optical fiber, comprising:
  detecting the location of the flaw along the fiber, and
  automatically inspecting the fiber at its detected flaw location in response to said detection to classify the flaw, the classification process comprising:
    determining the nominal boundary of the fiber in the vicinity of the flaw,
    determining the actual boundary of the fiber in the vicinity of the flaw,
    determining the differential between the nominal and actual fiber boundaries over at least a portion of the flaw, and
    classifying said flaw based upon said differential.

34. The method of claim 33, wherein the flaw location is detected at a first station, said automatic inspection is performed at a second station, and the fiber is advanced so that the flaw location moves from the first to the second station and is inspected at said second station in response to said flaw detection.

35. The method of claim 33, wherein said flaw is detected by transmitting a laser beam generally orthogonally through the fiber and detecting the beam after said transmission, and said fiber inspection is performed by backlighting the fiber in the vicinity of the flaw location, obtaining an image of the backlit fiber, and operating upon said image to classify the flaw.

36. The method of claim 35, wherein said fiber is further illuminated during said backlighting by a frontlight directed onto the fiber in the vicinity of the flaw location at an angle within the approximate range of 15°–30° to the fiber axis, and approximately coplanar therewith.

37. The method of claim 35, wherein said flaw is further classified by illuminating it with a focused light beam in a plane generally orthogonal to the backlighting direction, and observing the focused light beam reflectance pattern from the vicinity of the flaw.

38. The method of claim 37, wherein said focused light beam comprises a laser beam.

39. An automated method for detecting and classifying a flaw in an optical fiber, comprising:
  detecting the location of the flaw along the fiber, and
  automatically inspecting the fiber at its detected flaw location in response to said detection to classify the flaw as to type, the classification process comprising:
    determining actual and nominal boundaries of the fiber in the vicinity of the flaw comprising the steps of:
      illuminating the fiber in the vicinity of the flaw,
      obtaining a camera image of the illuminated fiber in the vicinity of the flaw, and
      pixelizing said image:
    generating differentials between spatial characteristics of said boundaries in said pixelized image along a path generally parallel to the fiber axis; and
    classifying said type of flaw based upon said differentials.

40. The method of claim 39, wherein the flaw location is detected at a first station, said automatic inspection is performed at a second station, and the fiber is advanced so that the flaw location moves from the first to the second station and is inspected at said second location in response to said flaw detection.

41. The method of claim 39, wherein said flaw is detected by transmitting a laser beam generally orthogonally through the fiber and detecting the beam after said transmission, and said fiber inspection is performed by backlighting the fiber in the vicinity of the flaw location, obtaining an image of the backlit fiber, and operating upon said image to classify the flaw.

42. The method of claim 41, wherein said flaw is further classified by illuminating it with a focused light beam in a plane generally orthogonal to the backlighting, and observing the focused beam reflectance pattern from the vicinity of the flaw.

43. The method of claim 41, wherein said fiber is further illuminated during said backlighting by a frontlight directed onto the fiber in the vicinity of the flaw location at an angle within the approximate range of 15°–30° to the fiber axis, and approximately coplanar therewith.

44. The method of claim 39, wherein said fiber is illuminated by transmitting light through it.

45. A method for detecting a splice in an optical fiber, comprising:
  illuminating the fiber with a focused light beam,
  observing the reflection of said focused beam from the fiber, and
  determining the presence or absence of a pair of spaced surface regions on the fiber that are generally orthogonal to the fiber axis and differ from the remainder of the fiber surface, with the presence of said regions corresponding to a splice.

46. The method of claim 45, wherein the focused beam is directed onto the fiber at an angle within the approximate range of 15°–45° to the fiber axis, and its reflectance is observed from an angle greater than 60° to the fiber axis.

47. The method of claim 45, wherein an image of the focused beam reflectance from the fiber is obtained and vertical regions therein are enhanced by processing the image through a Laplacian filter.

48. The method of claim 45, wherein said focused light beam comprises a laser beam.

* * * * *